(12) United States Patent
Egli et al.

(10) Patent No.: US 11,187,686 B2
(45) Date of Patent: Nov. 30, 2021

(54) CALIBRATING A GAS SENSOR

(71) Applicant: Sensirion AG, Stäfa (CH)

(72) Inventors: Daniel Egli, Stäfa (CH); Tobias Schoch, Stäfa (CH); Felix Hoehne, Stäfa (CH)

(73) Assignee: SENSIRION AG, Stafa (CH)

( * ) Notice: Subject to any disclaimer, the term of this patent is extended or adjusted under 35 U.S.C. 154(b) by 190 days.

(21) Appl. No.: 16/603,363

(22) PCT Filed: Apr. 5, 2018

(86) PCT No.: PCT/EP2018/058743
§ 371 (c)(1),
(2) Date: Oct. 7, 2019

(87) PCT Pub. No.: WO2018/185226
PCT Pub. Date: Oct. 11, 2018

(65) Prior Publication Data
US 2021/0088488 A1 Mar. 25, 2021

(30) Foreign Application Priority Data

Apr. 6, 2017 (EP) .................... 17165352

(51) Int. Cl.
*G01N 33/00* (2006.01)
*G01N 27/04* (2006.01)
*G01N 27/403* (2006.01)

(52) U.S. Cl.
CPC ......... *G01N 33/0006* (2013.01); *G01N 27/04* (2013.01); *G01N 27/403* (2013.01); *G01N 33/0027* (2013.01)

(58) Field of Classification Search
CPC .. G01N 33/0006; G01N 27/04; G01N 27/403; G01N 33/0027; G01N 33/0037;
(Continued)

(56) References Cited

U.S. PATENT DOCUMENTS 4,562,723 A * 1/1986 Hubner ................. G08B 19/00
340/633
5,007,283 A 4/1991 Ambos
(Continued)

FOREIGN PATENT DOCUMENTS

| GB | 2 254 696 A | 10/1992 |
|---|---|---|
| WO | 2008/045568 A2 | 4/2008 |
| WO | 2014/143175 A1 | 9/2014 |

OTHER PUBLICATIONS

A.. V. Shaposhnik et al., "Determination of Gases by a Combined Study of the Resistance and Noise Characteristics of Semiconductor Sensors", Journal of Analytical Chemistry, vol. 60, No. 4, 2005, pp. 369-372.
(Continued)

*Primary Examiner* — Robert R Raevis
(74) *Attorney, Agent, or Firm* — Ladas & Parry LLP

(57) ABSTRACT

A gas sensor includes a sensing element of a material including metal oxide and is sensitive to a target gas and to a recalibration gas different from the target gas. For recalibrating the gas sensor, a resistance of the sensing element is measured as an updated recalibration gas baseline resistance in a recalibration environment showing a recalibration gas baseline concentration.

20 Claims, 3 Drawing Sheets

(58) Field of Classification Search
CPC . G01N 33/0039; G01N 33/004; G01N 33/007
USPC ... 73/1.06, 23.2, 23.21, 31.01, 31.05, 31.06;
338/34; 324/691, 693, 730
See application file for complete search history.

(56) References Cited

U.S. PATENT DOCUMENTS

| | | |
|---|---|---|
| 6,872,599 B1 | 3/2005 | Li et al. |
| 7,023,074 B2 | 4/2006 | Li et al. |
| 7,413,934 B2 | 8/2008 | Tellkamp |
| 8,685,795 B2 | 4/2014 | Wang |
| 2004/0178082 A1 | 9/2004 | McDaniel |
| 2012/0192623 A1 | 8/2012 | Adami et al. |

OTHER PUBLICATIONS

ISR for International Application PCT/EP2018/058743, May 2018.
Extended European Search Report of EP17165352.0, dated Apr. 2017.
Diana H. Barnes, et al.: Hydrogen in the atmosphere: Observations above a forest canopy in a polluted environment: Journal of Geophysical Research, vol. 108, No. D6, 4197, doi:10.1029/2001JD001199, 2003.

* cited by examiner

CALIBRATING A GAS SENSOR

RELATED APPLICATION

This application is an application under 35 U.S.C. 371 of international Application No. PCT/EP2018/058743 filed on 5 Apr. 2018, which claims priority from EP Application No. 17165352.0 filed on 6 Apr. 2017, the disclosures of which are incorporated in their entirety by reference herein.

TECHNICAL FIELD

The invention refers to a method for operating a gas sensor, to a corresponding computer program element, and to a gas sensor.

BACKGROUND ART

Gas sensors containing a metal oxide (MOX) sensing element are widely used for gas measurements, e.g., in monitoring of indoor air quality by measuring volatile organic compounds, or in the monitoring of outdoor air quality by measuring one or more of CO, NO2, or O3. A metal oxide based gas sensor changes an electrical resistance of the sensing element, the material of which sensing element contains the metal oxide, as a function of a concentration of the gas desired to be detected, which gas is also referred to as target gas. A common problem of such gas sensors is that the absolute electrical resistance is not stable over time, which therefore does not allow a direct conversion of the measured resistance value into a corresponding target gas concentration value without unacceptable errors. This problem is usually solved by a baseline correction algorithm, which normalizes a measured resistance value to a baseline resistance. The baseline resistance is usually taken as the resistance of the sensing element in clean air, i.e. an air sample in which the target gas shows a defined background concentration that always is present in an environment the gas sensor operates in. Baseline and background are terms used interchangeable. In the event of an air sample that is contaminated with target gas, the target gas baseline concentration is significantly exceeded, and the absolute target gas concentration can be calculated dependent on a ratio of the target gas baseline resistance and the measured resistance.

However, this approach may have several disadvantages in many applications:

First, the target gas baseline gas concentration in "clean air", although very low, can vary significantly subject to the environment: For example, in applications monitoring indoor air quality, the target gas baseline concentration may vary from room to room subject, e.g. to outgassing materials present in the room which may represent an entire target range for target gas baseline concentrations. However, in such application, it is not desired to monitor variations in the target gas baseline concentrations but target gas concentrations of a bigger magnitude representing gas ingression into the room, for example, representing fire events, etc.

Due to the power law nature of a gas-concentration-to-resistance transfer function and the target gas baseline concentration, an error of a factor x in the target gas baseline concentration results also in the same error x of all measured gas concentrations. E.g. if the target gas baseline concentration is 0.1 ppm instead of 0.2 ppm, all gas sensor readings will be too large by a factor of 2, despite the rather small absolute error of 0.1 ppm of the target gas baseline concentration. As a result, MOX gas sensors that employ a target gas baseline correction cannot indicate absolute gas concentrations without the possibility of very large errors.

Second, a gas sensor that is operated in a high target gas concentration and that has not seen "clean air" before will interpret the high target gas concentration as clean air and adjust its baseline accordingly. As a result, the gas sensor readings will strongly underestimate the real target gas concentrations until the gas sensor has adapted itself to a "clean air" baseline.

DISCLOSURE OF THE INVENTION

The problem to be solved by the present invention is therefore to provide a method for operating a gas sensor as well as a gas sensor that allows identifying an absolute target gas concentration at a high accuracy.

According to a first aspect of the present invention, a method is provided for operating a gas sensor. The gas sensor comprises a sensing element of a material including or consisting of metal oxide that typically is to be heated to become operational to a temperature in a range between 100° C. and 400° C. subject to the material. The material selected for the sensitive element is sensitive to the target gas, and may be sensitive to multiple target gases, and also is sensitive to a recalibration gas.

In view of the fact that there is no defined constant baseline concentration for different locations on earth for many target gases, it is suggested to recalibrate the gas sensor instead to a gas referred to as recalibration gas that is different to the target gas and that, however, shows a defined constant baseline concentration in many different locations on earth, or a defined constant baseline concentration with respect to the gas sensor.

In a first embodiment, this recalibration gas is hydrogen. A baseline concentration for hydrogen is considered 0.5 ppm, see "Hydrogen in the Atmosphere: Observations above a forest canopy in a polluted environment", Barnes et al., Journal of Geophysical Research, Vol. 108, No. D6 4197, 2003. For the definition of the terms baseline concentration and baseline resistance it is referred to the "Background Art" section.

In a different embodiment, this recalibration gas is methane. A baseline concentration for methane is considered 1.77 ppm, see IPCC (Intergovernmental Panel on Climate Change) "Fifth Assessment Report: Climate Change 2014".

In a further embodiment, the gas sensor is arranged in or at a housing, and the recalibration gas is a background gas present in the housing. In one embodiment, the recalibration gas is represented by VOCs (Volatile Organic Compounds) that constantly may outgas from the housing and as such can perfectly serve as a baseline concentration. Specifically, the housing may be a housing of a device, and in particular of a portable device such as a smart phone or a portable electronic nose, and the recalibration gas is the background gas present in the housing of the device. In a different embodiment, the housing may be a housing of the gas sensor, and the recalibration gas is the background gas present in the housing of the gas sensor.

Accordingly, in a preferred embodiment, a recalibration gas baseline resistance is measured in a recalibration environment showing the recalibration background concentration.

It is preferred that a device containing the gas sensor automatically detects when the gas sensor is exposed to an environment qualifying as recalibration environment. In response to detecting the exposure of the gas sensor to an environment qualifying as recalibration environment the recalibrating step preferably is triggered. There are different ways to implement this triggering, and/or different data to derive this event from. In a first embodiment a sensor sensitive to ozone supports such automated detection. The appropriate recalibration environment may be detected when a signal of the ozone sensor indicates an ozone concentration exceeding a threshold, and/or when the signal of the ozone sensor indicates an increase in ozone concentration, the increase exceeding a threshold. Ozone is considered as an indicator for a suitable recalibration environment considered as "clean air" with e.g. hydrogen or methane dominating and other gases being absent or low concentrated.

Generally, and not limited to the ozone sensing approach, the recalibration environment may be considered as an outdoor environment with only little or no contamination of the "clean air" by other gases. In case the gas sensor and/or a device containing the gas sensor is a portable device such as a smart phone or a portable electronic nose, the detection of the recalibration environment may in particular be capable of distinguishing between an indoor environment less appropriate for recalibration in view of many gases present and an outdoor environment, which preferably is an outdoor environment absent contamination. In case the gas sensor and/or a device containing the gas sensor is a stationary device e.g. used indoor, the detection of the recalibration environment may in particular be capable of distinguishing between a contaminated indoor environment less appropriate for recalibration in view of many gases present and a non-contaminated indoor environment absent or with little contamination, such as e.g. after venting the room.

The above ozone sensor in one embodiment can be represented by a another sensing element of the gas sensor sensitive to ozone, in addition to the sensing element that is sensitive to the target gas other than ozone. In case of multiple sensing elements, all sensing elements may preferably be monolithically integrated on the same semiconductor chip, however, may have separate activation means such as heaters, or, in a different embodiments, may even have common activation means such as a common heater. Preferably, the at least two sensing elements contain metal oxide, however, preferably, of a different metal oxide material in order to encourage sensitivities to different gases.

In a different embodiment, a sensor supporting the automatic detection of a recalibration environment is sensitive to humidity. In a preferred embodiment, an absolute humidity calculated based on a relative humidity measurement and a corresponding temperature measurement preferably is lower outdoors than indoors such that the absolute humidity tailing below a threshold may indicate an outdoor environment suitable for recalibration, at least for some regions of the world. And/or the absolute humidity decreasing for more than a threshold may indicate so.

In a variant, a sensor sensitive to hydrogen may be provided, either as a separate sensor or as another sensing element of the gas sensor as is described above for the ozone sensor.

In a further variant, a sensor sensitive to methane may be provided, either as a separate sensor or as another sensing element of the gas sensor as is described above for the ozone sensor.

In particular when the gas sensor is arranged in or at a gas sensor housing, or is arranged in or at a housing of an electronic device, such housing may outgas over its lifetime which outgas, e.g. in form of VOCs, may serve as recalibration gas. This is in particular if the device is a portable device such as a smart phone or a portable electronic nose, given that the recalibration environment and recalibration gas is always present around the gas sensor.

In different embodiments, one or more sensors other than gas sensors may support the decision if a recalibration environment is considered as detected. Such sensor/s may also be referred to as context sensor/s providing information about the context the gas sensor and the corresponding device presently remain. The context in particular may include the location, and in particular may allow to distinguish between an indoor and an outdoor location in one embodiment. Such sensor preferably includes one of a GPS sensor indicating outdoor locations. Or, a light sensor such as a photodiode may be used e.g. to detect if the gas sensor or the corresponding device presently is in a pocket or accessible by fresh air.

Prior to the recalibration, and in particular between the first usage and the recalibration, the gas sensor preferably is operated based on an initial recalibration gas baseline resistance value. Such initial recalibration gas baseline value may in one embodiment be an assumed or estimated value stored in one of the gas sensor, a device containing the gas sensor, or in the cloud. In a different, embodiment, the initial recalibration gas baseline resistance value may be measured by the gas sensor in a calibration environment prior to shipping which calibration environment shows a recalibration gas baseline concentration dominating a target gas concentration. In another variant, a measurement of the initial recalibration gas baseline resistance may be taken by a different gas sensor e.g. a gas sensor of the same lot or manufacturing entity, for which gas sensors it can safely be assumed that they show a signal characteristic not deviating from each other significantly, such that the calibration parameters identified for one of the gas sensors at the same time can be applied to the other gas sensors. Given that one or the other gas sensor is expected to instantly be operable after shipping to a customer, it is preferred that this initial calibration is taken in an industrial calibration site, e.g. at the manufacturer, distributor or reseller, such as in a defined chamber, room or on an area of such site.

Preferably, in such calibration environment in which the constant baseline concentration in case of hydrogen can be assumed to be 0.5 ppm, in case of methane can be assumed to be 1.77 ppm, and in case of a VCO being specifically determined, the present concentration of the target gas is measured, too, which is referred to as target gas reference concentration in the following. This measurement preferably is performed by a different sensing means that is capable of sensing such reference quantities of the target gas, which different sensing means, such as a different gas sensor, may be provided in the calibration environment.

Preferably, both the initial recalibration gas baseline resistance, as well as the corresponding target gas reference concentration are stored, preferably in the gas sensor itself, or at a different location. In one embodiment, the gas sensor may include a gas sensor chip, wherein the sensing element is applied to a substrate such as a semiconductor substrate. In this embodiment, a processing unit may be integrated in the same gas sensor chip e.g. by CMOS processing which processing unit may also include a non-volatile storage for storing at least the values for the initial recalibration gas baseline resistance and the target gas reference concentration. Those values are used in operating the gas sensor later on to determine drift-free concentration values of the target gas. The processing unit in a different embodiment may be implemented in a memory of an IC chip different to the gas sensor chip, in a memory of a different processing unit, in a memory provided in a device comprising the gas sensor, or in a memory remote from the gas sensor, preferably a memory in a server representing the cloud. All these variants are also applicable to storing the recalibration gas baseline resistance updated in the various recalibration steps applied ever operating time of the gas sensor.

In a recalibration measurement in a recalibration environment also referred to as clean air environment with an expected hydrogen, methane or other recalibration/background gas baseline concentration, the associated electrical resistance of the sensing element is measured. Based on this measured recalibration gas baseline resistance and the known corresponding concentration of the target gas present in such recalibration environment, and based on a measured resistance in a measuring environment, a target gas concentration in the measurement environment can be determined.

The recalibration environment, hence, is also expected to show a target gas concentration that can be considered in a baseline range although as mentioned above, a well-defined value may not exist. The baseline range is complementary to a target range, being defined by target gas concentrations expected during operations. Given that for a first class of target gases such as VOCs (Volatile Organic Compounds) or carbon monoxide, a gas sensing element comprising metal oxide shows higher resistance values the lower the target gas concentrations are, it is preferred that the target range of resistances measured during operation is lower than the baseline range that represents baseline target gas concentrations. However, for a second class of target gases such as NO2, a gas sensing element comprising metal oxide shows lower resistance values the lower the target gas concentrations are, it is preferred that the target range of resistances measured during operation is higher than the baseline range that represents baseline target gas concentrations.

In a preferred embodiment, one or more additional measurements are taken by the subject gas sensor or by an assigned gas sensor for determining calibration parameters for calibrating the gas sensor: For example, one or more resistances may be measured at different target gas concentrations in the target range. Such additional measurements may help complete the resistance—target gas concentration characteristic. Such target gas concentrations may be provided into a calibration environment, and may be known up-front or can be measured by a different gas sensor. It is noted that such measurements are taken at various target gas concentrations, while the recalibration gas concentration remains at its baseline during these measurements. Calibration parameters such as the power n of the target concentration being proportional to the measured resistance may be calculated from the results of the various measurements and preferably are stored in one of the memories introduced above.

Based on the measurement of the recalibration gas baseline resistance, and based on one or more measurements identifying one or more additional resistances corresponding to different target gas concentrations, a characteristic can be determined for assigning target gas concentrations to measured resistances. Such characteristics may be stored as a formula of a target gas concentration=$f$(measured resistance), or may be stored as a curve or a look-up-table, each providing an assignment between target gas concentration and measured resistance. In general, such characteristics includes calibration parameters, one of which is the recalibration gas baseline resistance updated in various recalibration steps over time. This allows a recalibration by simply measuring a present recalibration gas baseline resistance.

During normal operation of the gas sensor, the concentration of the target gas in an environment of the gas sensor includes measuring the resistance of the sensing element and determining the concentration of the target gas at least dependent on the measured resistance and dependent on the recalibration gas baseline resistance measured in the most previous recalibration step.

Given that the gas sensor may show drift over time some ongoing recalibration may be necessary. As indicated above, a (re-)calibration with respect to a baseline target gas concentration is difficult to achieve in view of no constant baseline target gas concentration being applicable to many target gases and even minor changes in baseline target gas concentrations may have considerable impact on the interpretation of the target gas concentrations. Especially for recalibration purposes, it is advantageous to instead determine the recalibration gas baseline resistance from new which may be found either anywhere on earth in view of the constant baseline hydrogen or methane concentration of 0.5 ppm or 1.77 ppm respectively, or at any place in case a device the gas sensor is arranged in is considered as recalibration environment in view of a constant outgassing from materials the device is built from such as the housing or a PCB, however, preferably in an environment that is dominated by the recalibration gas in order to exclude a significant impact on the measured recalibration gas baseline resistance resulting from the target gas. The recalibration is required since the gas sensor may drift over time and may show a varying recalibration gas baseline resistance over time.

Accordingly, for recalibration purposes, a recalibration gas baseline resistance is measured in a recalibration environment showing a recalibration gas baseline concentration. This recalibration gas baseline resistance now represents the target gas reference concentration initially determined or estimated given that the gas sensor does not drift different for the recalibration gas and the target gas.

Hence, after having measured the recalibration gas baseline resistance, in any subsequent determination of a target gas concentration, the target gas concentration can be determined dependent on the then measured resistance and this latest measured recalibration gas baseline resistance.

For determining a suitable point in time for measuring the updated recalibration gas baseline resistance, the following retrospective approach is an alternative to another sensor triggering the recalibration: Given that the gas sensor does not know when it is arranged in an environment that allows for a recalibration, and hence an environment that is dominated by the constant recalibration gas baseline concentration, measured resistances of the past are preferably evaluated. Here, it is preferred that out of a set of resistances measured by the sensing element in the past and preferably stored in a memory of the gas sensor or elsewhere, a single resistance value is selected, that indicates a dominant recalibration gas baseline concentration. As a result, the environment in which this resistance was measured is considered as recalibration environment. And, preferably, this measured resistance is used as updated recalibration gas baseline resistance.

Preferably, this resistance is the maximum resistance out of the set given that for a first class of target gases including VOCs a resistance of the sensing element containing metal oxide decreases at increasing concentration of a gas. Therefore, the resistance selected as updated hydrogen or methane baseline resistance is the resistance showing a maximum value out of the resistances of the set since it represents the lowest gas concentration that in this case if the lowest concentration of hydrogen or methane respectively.

In this regard, it is preferred that the set of measured resistances that is evaluated for e.g. identifying the maximum resistance value is at maximum limited to resistances measured and stored since the beginning of operative readings of the gas sensor in case no previous recalibration was performed so far, or is at maximum limited to resistances measured and stored since the most recent recalibration. However, preferably, a subset of these resistance values may only be evaluated for identifying the maximum value, e.g. only the most recent x resistance values, etc. In a different embodiment, the recalibration may automatically be triggered, e.g. subject to the time passed since the most previous recalibration, or dependent on the heating time of the gas sensor, e.g. when the heating time exceeds a threshold, e.g. when it may be assumed that the heating causes drift. Such trigger for starting a recalibration may also set the starting point for measurements to be considered for selecting the maximum value of.

For a second class of target gases, such as $NO_2$, the characteristics of the metal oxide based sensing element is the opposite such that for increasing target gas concentrations the resistance of the sensing element increases, too. In view of this, the lowest resistance value out of the set may be selected as measured hydrogen, methane or VOC baseline resistance value.

Preferably, the material of the sensing element is selected such that for a target range of the target gas concentration a sensor response of the sensing element exceeds the sensor response for a recalibration gas concentration in its baseline range, and wherein the sensor response for a baseline range of the target gas concentration is less than the sensor response of the sensing element for the recalibration gas in its baseline range. In other words, for low recalibration gas concentrations that coincide with a low baseline range of target gas concentrations e.g. in clean air, the sensing element predominantly reacts to these recalibration gas concentrations and only to a less extent to target gas concentrations, such that whenever a high resistance is measured, it can safely be assumed that this stems from a recalibration environment dominated by the recalibration gas. However, for the target range of target gas concentrations, i.e. a range of target gas concentrations that the gas sensor is assumed to be exposed to during operation, and specifically during events coinciding with high target gas concentrations way above the baseline range of the target gas, the sensing element predominantly reacts to these high target gas concentrations and only to a less extent to the low or moderate concentrations of the recalibration gas, such that whenever a low resistance is measured, it can safely be assumed that this stems from an increased target gas concentration in the environment.

Preferably, a suitable MOX material is selected for the sensing element. Preferably, a relative sensor response of the recalibration gas and the target gas(es) is adjusted by selecting the material of the sensing element appropriately. This supports, that when the gas sensor is exposed to "clean air" the sensor response, i.e. the measured resistance value, is dominantly determined by the response to 0.5 ppm hydrogen, for example. E.g., for an indoor air quality total VOC (Volatile Organic Compound) target gas sensor application, typical total VOC concentrations in clean air are below 0.5 ppm or even below 0.2 ppm. Therefore, the MOX sensing material preferably is chosen such that the sensor response to 0.5 ppm $H_2$ is stronger compared to 0.2 or even 0.5 ppm of total VOCs.

However, at the total target gas concentrations of interest in the application, i.e. the target range for the target gas concentrations, e.g. >1 ppm for VOC, the sensor response preferably is dominated by the sensor response to the target gas, e.g. the VOCs, and not by the response to 0.5 ppm hydrogen in case of hydrogen being used as recalibration gas. As a consequence, there is an optimum in the response of the sensor to the target gas(es) relative to the response to 0.5 ppm of hydrogen and the MOX sensing material preferably is optimized accordingly.

Preferably, the material of the sensing element is doped for tuning the sensitivities of the sensing element versus the recalibration gas on the one hand, and the one or more target gases on the other hand.

As an example for the indoor air quality application described above, a sensing element material of Pd-doped $SnO_2$ with approx. 1% Pd can be used. The sensing material preferably is deposited as a 10 μm thick layer on a micro hotplate with Pt electrodes for electrical contact. The gas sensor preferably is operated at a hotplate temperature of 300° C.-400° C. For this gas sensor, the sensor response to 0.5 ppm hydrogen may be equal to the response to 0.5 ppm Ethanol which is used as a proxy for VOCs.

For an application with higher target gas concentrations, e.g. an alcohol tester, it is preferable to have a larger sensor response to $H_2$ compared to VOCs in order to increase the probability that the sensor is exposed to clean air. This is achieved by increasing the Pd doping level of the $SnO_2$, e.g. to 3% Pd.

According to another aspect of the present invention, a computer program element is provided comprising computer program code means performing a method according to any of the previous embodiments of the method.

According to a further aspect of the present invention, a gas sensor is provided comprising a sensing element of a material including metal oxide and being sensitive to a target gas and to a recalibration gas different from the target gas. A processing unit is provided for executing the steps of a method according to any of the previous embodiments.

Other advantageous embodiments are listed in the dependent claims as well as in the description below. All the various embodiments may be applicable to each of the aspects, i.e. the method, the gas sensor and the computer program element.

BRIEF DESCRIPTION OF THE DRAWINGS

Embodiments of invention will be better understood from the following detailed description thereof. Such description makes reference to the annexed drawings, wherein.

MODES FOR CARRYING OUT THE INVENTION

More general embodiments precede the embodiments illustrated in connection with the Figures. In the following embodiment of a method for operating a gas sensor, gas sensor calibration parameters are determined for Hydrogen and one or several target gases, like e.g., Formaldehyde, Toluene, Ethanol, CO, O3, NO2, . . . . The calibration parameters can be determined for the gas sensor type, for each batch of gas sensors manufactured together, or for each individual gas sensor. Preferably, these parameters are stored in a non-volatile memory on the gas sensor itself or on an additional microprocessor used to convert the measured resistances of the sensing element of the gas sensor into target gas concentrations. In particular, and predating the regular operation of the gas sensor the resistance value of 0.5 ppm Hydrogen or of a baseline concentration of another recalibration gas is measured or estimated and stored as initial recalibration gas baseline resistance $R_{IniBaseRG}$ as well as the concentration $c_{ref}$ of the target gas that corresponds to $R_{IniBaseRG}$.

During the operation of the gas sensor, all resistances measured $R_{sens}$ are evaluated as a ratio between the initial recalibration gas baseline resistance $R_{IniBaseRG}$, and later on the measured recalibration gas baseline resistance $R_{BaseRG}$ replacing the initial recalibration gas baseline resistance $R_{IniBaseRG}$, and the measured resistance value $R_{sens}$. By adjusting the recalibration gas baseline resistance $R_{BaseRG}$ over the lifetime of the gas sensor triggered by a different sensor, or by using a suitable algorithm, e.g., setting $R_{BaseRG}$ equal to the highest resistance the gas sensor has measured since the last recalibration, errors induced by a drift of the sensing element resistance can be compensated.

Since the target gas concentration $c_{ref}$ corresponding to $R_{BaseRG}$ is known, the gas sensor readings can be given as absolute concentrations without introducing the unacceptable errors.

The following Figures describe embodiments using hydrogen as recalibration gas. However, it is understood that any other suitable recalibration gas such as methane, or VCOs in a housed application may be used instead.

Figure 1:
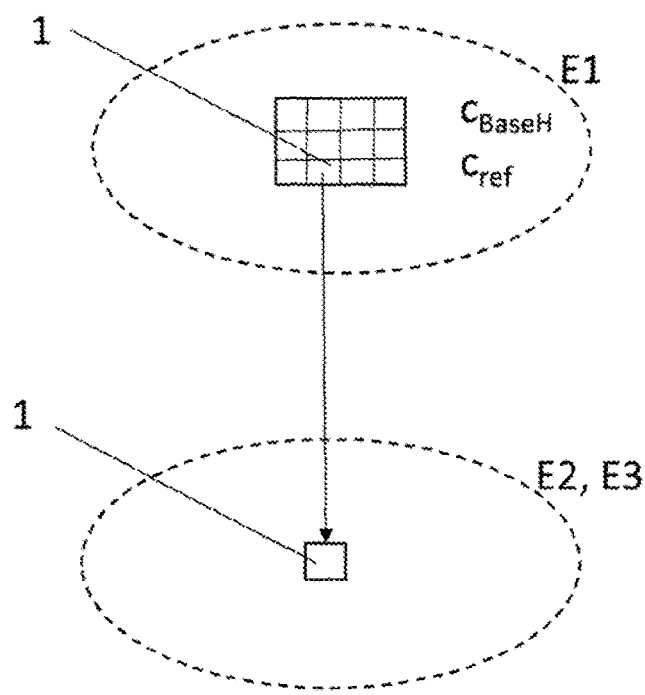
FIG. 1 illustrates a scenario representing a method according to an embodiment of the present invention.

FIG. 1 illustrates a scenario representing a method according to an embodiment of the present invention. A batch of sensors 1 manufactured at a manufacturing site is represented by a set of rectangles. The batch of sensors 1 presently still is present in an industrial site, and specifically in a calibration location of such industrial site providing a calibration environment E1 at least with respect to hydrogen concentration. The hydrogen concentration in such calibration environment E1 is expected to be a baseline hydrogen concentration $c_{BaseH}$. Presently, the concentration of the target gas $c_{ref}$ is not known yet but is measured by a separate gas sensing means sensitive to the target gas. The resistance of the gas sensor identified by reference numeral 1, by another gas sensor of the same batch, or by each gas sensor 1 of the batch is measured as initial baseline hydrogen resistance $R_{IniBaseH}$, and preferably stored in each or the corresponding gas sensor 1 respectively. The target gas reference concentration $c_{ref}$ is stored in each of the gas sensors 1, too.

The arrow indicates a subsequent shipping of the gas sensors 1 to customers where a gas sensor 1 is operated in the following in a defined application in an operating environment E2, also referred to as measurement environment. For example, the present gas sensor 1 may be arranged in a room of a building for detecting indoor air quality. Accordingly, the gas sensor 1 may, for example, be sensitive to one or more of the target gases such as VOCs. This may be achieved by a single sensing layer in the gas sensor of a dedicated metal oxide material, or by multiple sensing elements in the gas sensor 1, each of the sensing elements being receptive to one or more different target gases.

In the operating environment E2 a target gas concentration $c_{sens}$ prevails, and the gas sensor 1 takes measurements, e.g. on a regular basis. Hence, the resistance $R_{sens}$ of the sensing element is measured, and the corresponding target gas concentration $c_{sens}$ is determined dependent on at least the stored initial baseline hydrogen resistance $R_{IniBaseH}$, the corresponding target gas reference concentration $c_{ref}$, and the measured resistance $R_{sens}$.

At some point in time, it may be desired to recalibrate the gas sensor 1. For this purpose, an environment E3 suitable for recalibration is required. There may be periods in time with no increased target gas concentrations in the operating environment E2, such that the very same operating environment E2 is suited as recalibrating environment E3 at a different point in time. In particular, at such point in time the target gas concentration is in a baseline range. According to the set-up of the sensing element sensitivity, in such scenario the hydrogen dominates the resistance of the sensing element over the target gas, such that the measured resistance in such environment E3 may be used as measured hydrogen baseline resistance $R_{BaseH}$. The point in time when preferably taking such recalibration measurement is explained in more detail in connection with FIG. 3.

Subsequent to the recalibration, the concentration of the target gas in the operating environment E2 now is determined dependent on the then measured resistance of the gas sensor, and at least on the measured hydrogen baseline resistance $R_{BaseH}$, that is stored in the gas sensor 1.

Figure 2:
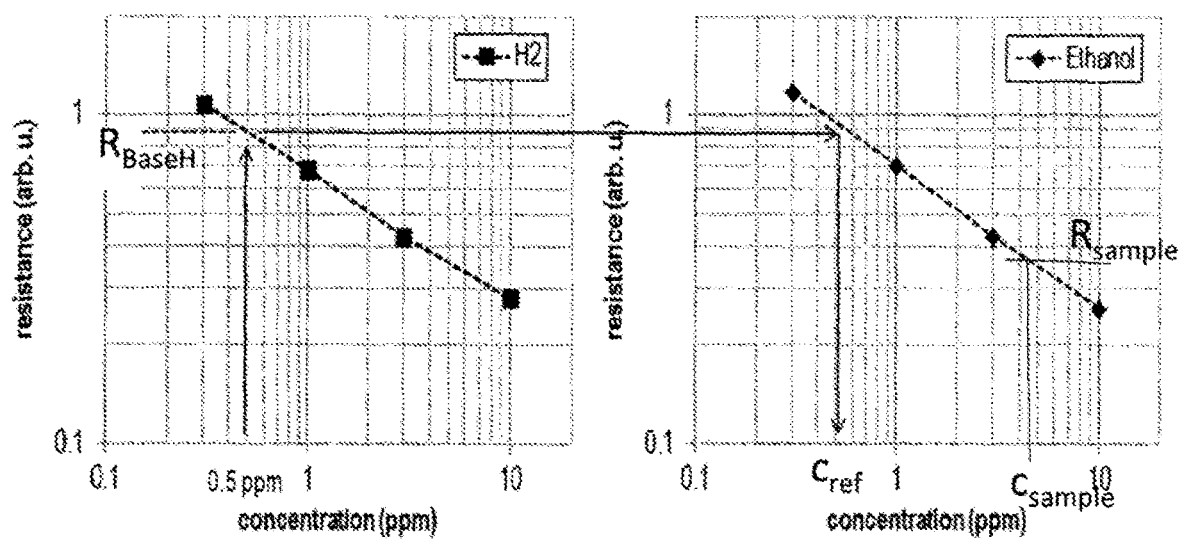
FIG. 2 illustrates characteristics of the gas sensor supporting a method according to an embodiment of the present invention.

FIG. 2 illustrates responses of the gas sensor, i.e. resistance values R of the associate sensing element, for different concentrations of Hydrogen H2 (left panel) and Ethanol (right panel). During the initial calibration of the gas sensor, e.g. at an industrial site, the gas sensor is exposed to clean air including a baseline hydrogen concentration $c_{BaseH}$, and a corresponding resistance is measured and stored as initial hydrogen baseline resistance $R_{IniBaseH}$. Given that for the present material of the sensing element in low ranges of target gas concentrations the sensitivity of the material to hydrogen dominates, the measured hydrogen baseline resistance does not reflect the present (low) target gas concentration, e.g. the concentration of Ethanol. For this reason, the present concentration of the target gas in this calibration environment is measured by a separate gas sensor, and is stored as reference target gas concentration $c_{ref}$. Hence, the initial hydrogen baseline resistance $R_{IniBaseH}$ and the reference target gas concentration $c_{ref}$ are related. Any further resistance measurement hence can be related to the initial hydrogen baseline resistance $R_{IniBaseH}$.

Preferably, an entire characteristic between the measured resistances $R_{sens}$ and the associate target gas concentrations $c_{sens}$ is determined during the calibration on the industrial site. Under the assumption of the R/c characteristic following the power law:

$$R_{sens} = R_0 * c_{sens}^n \qquad (1)$$

wherein $R_{sens}$ is the resistance of the metal oxide sensing element as measured, in response to a concentration $c_{sens}$ of the target gas, n is the power of $c_{sens}$ (to be determined), and R0 is a parameter (to be determined).

In a first step, preferably on an industrial site, the target gas calibration parameters $R_0$ and n are determined. This preferably is achieved by the or a different gas sensor of the same kind being exposed to two different target gas concentrations sensor, and the resistance $R_{sens}$ of the subject gas sensor is measured for each.

In a next step, the gas sensor is brought to a calibration environment showing a hydrogen baseline concentration $c_{BaseH}=0.5$ ppm hydrogen. The corresponding measured hydrogen baseline resistance $R_{BaseH}$ is measured. Note that in the above context this initial hydrogen baseline resistance previously was referred to by $R_{IniBaseH}$ which is now referred to as $R_{BaseH}$ instead given that it facilitates reading the following formulas. Based on this measurement, a target gas concentration $c_{ref}$ that corresponds to the initial hydrogen baseline resistance $R_{BaseH}$ is calculated by $$c_{ref}=(R_{BaseH}/R_0)^{1/n} \quad (2)$$

$R_{BaseH}$ is determined by measuring the sensor resistance at 0.5 ppm hydrogen as laid out above, and $R_0$ and n are known from the first step.

The target gas concentration $c_{sens}$ for a subsequent measurement is given by $$c_{sens}=c_{ref}*(R_{sens}/R_{BaseH})^{1/n} \quad (3)$$

The parameters n and $c_{ref}$ are the calibration parameters which are known, see above, and which are preferably stored on the gas sensor or on a microprocessor or in the cloud. $R_{BaseH}$, however, is considered to be the parameter that is continuously updated and as such represents a continuously updated hydrogen baseline resistance value.

It is preferable to store an initial value of $R_{BaseH}$ on the sensor/microprocessor but not necessary. In a basic version, $R_{BaseH}$ can be determined when the device is operated in the field with the disadvantage that the readings are only meaningful after a suitable value of $R_{BaseH}$ has been measured.

Accordingly, the calibration characteristic as shown on the right hand panel preferably can be stored in form of formula (3) in the gas sensor 1, including the values for the $R_{BaseH}$, $c_{ref}$, which can be regarded gas calibration parameters. Any term supporting the function $c_{sens}=f(R_{sens})$ can be considered as calibration parameter/s.

At a later stage, upon recalibrating the gas sensor 1 in the operating environment E3, it is sufficient to only measure a then current hydrogen baseline resistance $R_{BaseH}$.

Figure 3:
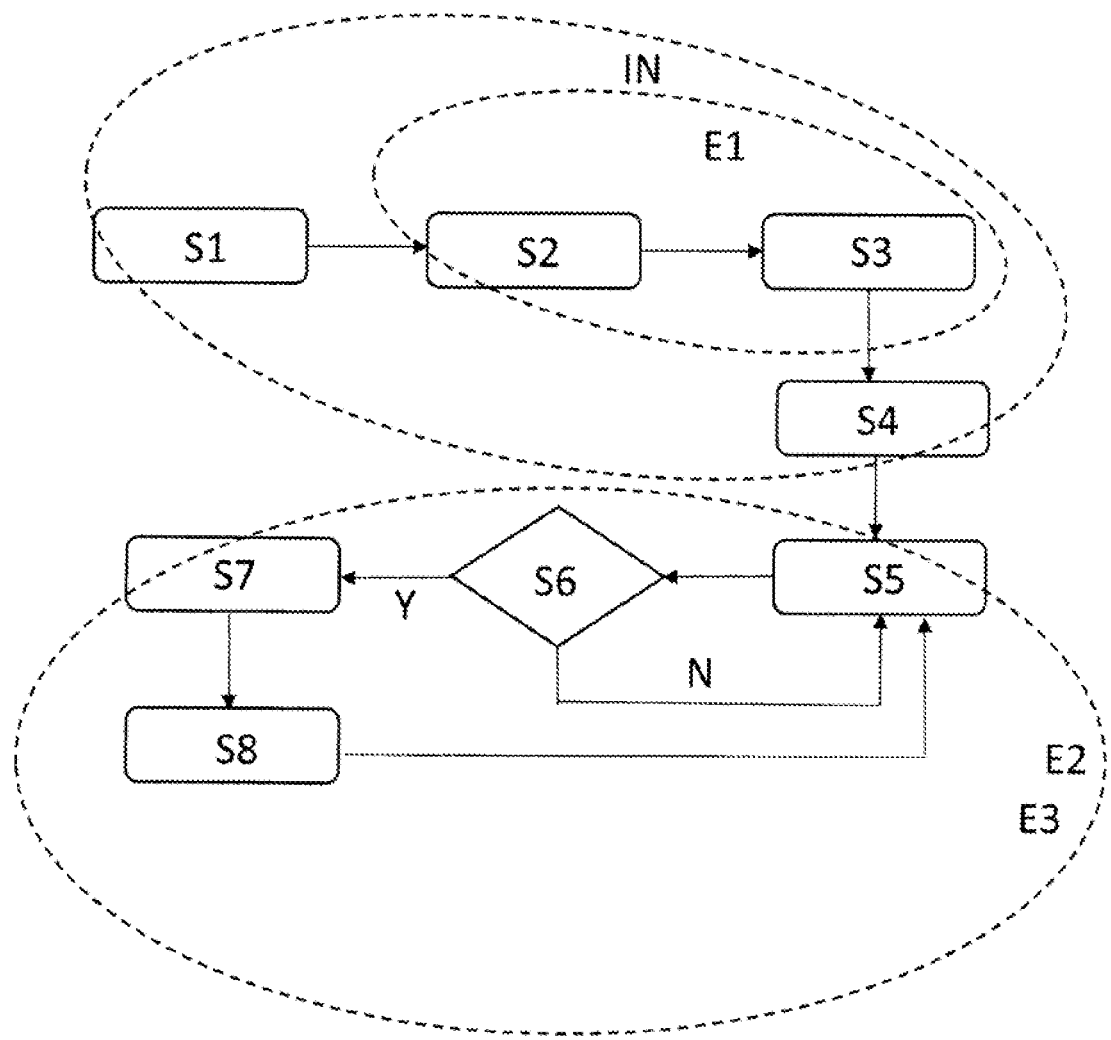
FIG. 3 illustrates a flowchart representing a method according to an embodiment of the present invention.
Figure 4:
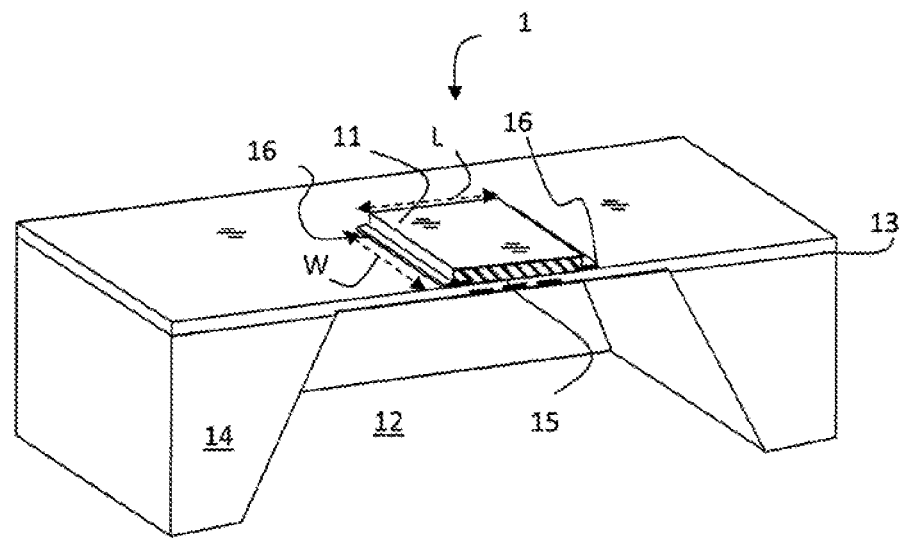
FIG. 4 shows a schematic perspective view of a metal oxide gas sensor according to an embodiment of the present invention.
Figure 5:
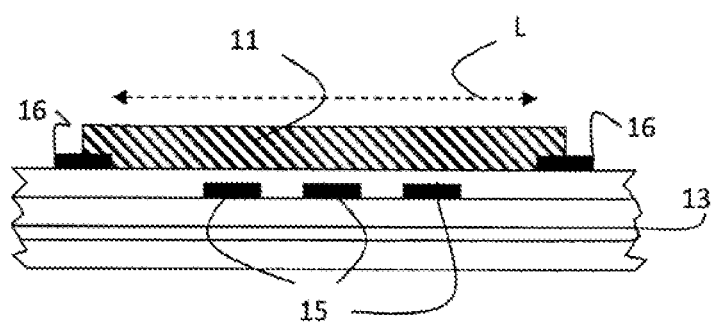
FIG. 5 illustrates an enlarged section of the gas sensor of FIG. 4 in cross cut.

FIG. 3 illustrates a flowchart representing a method according to an embodiment of the present invention. The first four steps S1 to S4 are performed on an industrial site IN: In step S1, a gas sensor 1 as is shown e.g. in FIGS. 4 and 5 is manufactured. In step S2, the gas sensor 1 or a different gas senor of the same type is exposed to a calibration environment E1, e.g. clean air, which calibration environment E1 shows a hydrogen baseline concentration of 0.5 ppm, and a target gas concentration in a baseline target gas range significantly lower than the operational target gas concentrations expected to be measured. The corresponding initial hydrogen baseline resistance $R_{IniBaseH}$ of the sensing element of the gas sensor is measured in this calibration environment E1 in step S2. In step S3, the target gas reference concentration $c_{ref}$ is measured in the calibration environment E1. In step S4, the initial hydrogen baseline resistance $R_{IniBaseH}$ and the target gas reference concentration $c_{ref}$ are stored in the gas sensor 1, and preferably a calibration characteristic as shown in the right hand panel of FIG. 2 is stored in form of one of a formula, a characteristic or a lock-up-table in the gas sensor. The corresponding measurements can be conducted in the calibration environment E1 by supplying known or measured concentrations of the target gas into the calibration environment E1.

Upon delivery, the gas sensor 1 enters into its operational environment E2, in which the gas sensor is envisaged to take measurements of target gas concentrations. These measurements are performed over time in step S5. In step S6, it is evaluated, if, for example, the operational age of the gas sensor, or its accumulated heating time exceeds a threshold, or a trigger is received which then advises to start a recalibration. If no such recalibration scenario is advised (N), measurements continue based on the present calibration parameters. In case a recalibration is advised (Y), a hydrogen baseline resistance $R_{BaseH}$ is measured in step S7. In step 38, the hydrogen baseline resistance is stored and replaces any previous (initial) hydrogen baseline resistance value $R_{BaseH}$ and is used in the subsequent determinations of target gas concentrations $c_{sens}$ be derived from the measured resistances in step S5.

FIG. 4 illustrates a gas sensor 1 according to an embodiment of the invention, the gas sensor 1 comprising a sensing element 11. The sensing element 11 is of or at least comprises a metal oxide material. The sensing element 11 is arranged on a semiconductor chip comprising a semiconductor substrate 14 and CMOS layers 13 deposited thereon. Preferably, however not shown in FIG. 4, electronic circuitry is integrated in the chip, preferably representing a processing unit executing a method according to an embodiment of the present invention. Parts of the CMOS layers 13 and the semiconductor substrate 14 are etched away to form a MEMS device with a cavity 12 at the location of the sensing element 11. The remaining layers 13 form a thin membrane to support the actual sensing element 11.

As can be derived from an enlarged cross cut view of a section of the membrane, conducting elements forming a heater 15 are embedded in the CMOS layers 13. The heater 15 is provided to heat the metal oxide sensing element 11 during operation of the gas sensor. The membrane structure provides an inherent thermal insulation for the rest, of the substrate including the processing unit. As a result, the temperature can rise rapidly around the metal oxide sensing element 11, while the thicker part of chip reacts due to its thermal inertia with a slower rise of temperature. By controlling the heater 15 accordingly, the metal oxide sensing element 11 can be heated to its operating temperature of 100 to 400 degrees Celsius. Only at such an operating temperature, the sensing element 11 becomes sensitive to the one or more target gases and/or hydrogen.

The metal oxide sensing element 11 is contacted by two conductive electrodes 16 and hence acts as a resistor. In the presence of an analyte representing a target gas the resistance of the sensing element 11 between the electrodes 16 changes thereby providing a measure of the concentration of the target gas in the immediate vicinity of the gas sensor 1.

The invention claimed is:

1. Method for operating a gas sensor comprising a sensing element of a material including metal oxide and being sensitive to a target gas and to a recalibration gas different from the target gas, the method comprising the step of:
    recalibrating the gas sensor in a recalibration environment showing a recalibration gas baseline concentration
    wherein
        the material of the sensing element is such that
            for a target gas concentration in a target range a sensor response of the sensing element exceeds its sensor response for a recalibration gas concentration in a baseline range, and for a target gas concentration in a baseline range the sensor response of the sensing element is less than its sensor response for a recalibration gas concentration in the baseline range.

2. Method according to claim 1, wherein the recalibration gas is one of hydrogen or methane.

3. Method according to claim 1,
wherein the gas sensor is arranged in or at a housing,
wherein the recalibration gas is a background gas present in the housing.

4. Method according to claim 3 wherein at least one of:
the housing is a housing of a device, and wherein the recalibration gas is a background gas present in the housing of the device,
the housing is a housing of the gas sensor, and wherein the recalibration gas is a background gas present in the housing of the gas sensor.

5. Method according to claim 1 comprising the steps of:
for identifying a concentration of the target gas in an environment of the gas sensor: measuring a resistance of the sensing element, and determining the concentration of the target gas dependent on the measured resistance and dependent on an initial recalibration gas baseline resistance value,
for recalibrating the gas sensor: measuring a recalibration gas baseline resistance of the sensing element in the recalibration environment,
for identifying a concentration of the target gas in an environment of the gas sensor subsequent to recalibrating the gas sensor measuring a resistance of the sensing element, and determining the concentration of the target gas dependent on the measured resistance and dependent on the recalibration gas baseline resistance.

6. Method according to claim 5,
wherein the measured recalibration gas baseline resistance is stored in one of:
a memory of a semiconductor chip including the sensing element;
a memory of a microprocessor implemented in a semiconductor chip separate from a semiconductor chip including the sensing element;
a memory provided in a device comprising the gas sensor;
a memory remote from the gas sensor.

7. Method according to claim 1, comprising
automatically detecting when the gas sensor is exposed to an environment qualifying as recalibration environment, and
in response to detecting the exposure of the gas sensor to an environment qualifying as recalibration environment triggering the recalibrating step.

8. Method according to claim 7,
wherein the exposure of the gas sensor to an environment qualifying as recalibration environment is detected dependent on one or more of:
a signal of a sensor sensitive to ozone,
on a signal of a sensor sensitive to humidity, and
on a signal of a sensor insensitive to a gas concentration.

9. Method according to claim 7,
wherein the exposure of the gas sensor to an environment qualifying as recalibration environment is detected dependent on one or more of:
a signal of a sensor sensitive to hydrogen, and
a signal of a sensor sensitive to methane.

10. Method according to claim 7,
wherein the exposure of the gas sensor to an environment qualifying as recalibration environment is detected dependent on one or more of:
a signal of a sensor sensitive to ozone,
wherein the sensor sensitive to ozone is represented by another sensing element of the gas sensor,
wherein the exposure of the gas sensor to the environment qualifying as recalibration environment is detected dependent on one or more of the signal of the ozone sensor indicating an ozone concentration exceeding a threshold, or the signal of the ozone sensor indicating an increase in ozone concentration the increase exceeding a threshold,
on a signal of a sensor sensitive to humidity,
wherein the sensor sensitive to humidity is represented by another sensing element of the gas sensor
wherein the exposure of the gas sensor to the environment qualifying as recalibration environment is detected dependent on one or more of an absolute humidity derived from the signal of the humidity sensor falling below a threshold, or a decrease in absolute humidity derived from the signal of the humidity sensor the decrease exceeding a threshold, and
on a signal of a sensor insensitive to a gas concentration,
wherein the sensor includes one of a GPS sensor, a light sensor,
wherein the exposure of the gas sensor to the environment qualifying as recalibration environment is detected dependent on the signal of the GPS sensor detecting an outdoor location.

11. Method according to claim 7,
wherein the exposure of the gas sensor to an environment qualifying as recalibration environment is detected dependent on one or more of:
a signal of a sensor sensitive to hydrogen,
wherein the sensor sensitive to hydrogen is represented by another sensing element of the gas sensor,
wherein the exposure of the gas sensor to the environment qualifying as recalibration environment is detected dependent on one or more of the signal of the hydrogen sensor indicating a hydrogen concentration below a threshold, or the signal of the hydrogen sensor indicating a decrease in hydrogen concentration the decrease rate exceeding a threshold, and
a signal of a sensor sensitive to methane,
wherein the sensor sensitive to methane is represented by another sensing element of the gas sensor,
wherein the exposure of the gas sensor to the environment qualifying as recalibration environment is detected dependent on one or more of the signal of the methane sensor indicating a methane concentration below a threshold, or the signal of the methane sensor indicating a decrease in methane concentration the decrease rate exceeding a threshold.

12. Method according to claim 1, comprising
determining a calibration characteristic of the gas sensor, and
determining a reference concentration of the target gas in an environment showing the recalibration gas baseline concentration ($c_{BaseRG}$) resulting in the initial recalibration gas baseline resistance value.

13. Method according to claim 1,
wherein in the recalibrating step, a resistance value is selected as recalibration gas baseline resistance out of a set of resistances measured in the past.

14. Method according to claim 13,
wherein for a first class of target gases the resistance of the sensing element decreases at increasing concentration (c) of the target gas,
wherein the selected resistance is the resistance showing a maximum value out of the resistances of the set.

15. Method according to claim 14,
wherein for a second class of target gases the resistance of the sensing element increases at increasing concentration of the target gas and the selected resistance is the resistance showing a minimum value out of the resistances of the set.

16. Method according to claim 13, wherein the set of resistances measured in the past is limited to resistances measured since the most recent recalibration respectively, and the set of resistances represents a subset of resistances measured since the most recent recalibration.

17. Method according to claim 1, wherein the resistance of the sensing element of the gas sensor is proportional to a power n of the concentration of the target gas.

18. Method according to claim 17, wherein the power n and other parameters if applicable are determined by taking a sufficient number of measurements of the resistance of the sensing element or a sensing element of a gas sensor of the same kind at different target gas concentrations.

19. A non-transitory computer-readable storage medium, comprising computer program element which when run on a processing unit
recalibrates a gas sensor in a recalibration environment showing a recalibration gas baseline concentration
wherein
the sensor comprises a sensing element comprising a material such that
for a target gas concentration in a target range a sensor response of the sensing element exceeds its sensor response for a recalibration gas concentration in a baseline range, and
for a target gas concentration in a baseline range the sensor response of the sensing element is less than its sensor response for a recalibration gas concentration in the baseline range.

20. Gas sensor, comprising
a sensing element of a material including metal oxide and being sensitive to a target gas and to a recalibration gas different from the target gas, and
a processing unit programmed to recalibrate the gas sensor in a recalibration environment showing a recalibration gas baseline concentration
wherein
the material of the sensing element is such that
for a target gas concentration in a target range a sensor response of the sensing element exceeds its sensor response for a recalibration gas concentration in a baseline range, and
for a target gas concentration in a baseline range the sensor response of the sensing element is less than its sensor response for a recalibration gas concentration in the baseline range.

* * * * *